United States Patent
Braun et al.

(10) Patent No.: US 6,521,199 B2
(45) Date of Patent: Feb. 18, 2003

(54) REGENERATION OF ONIUM FLUORIDE-HF ADDUCTS

(75) Inventors: Max Braun, Wedemark (DE); Stefan Palsherm, Barsinghausen (DE)

(73) Assignee: Solvay Fluor und Derivate GmbH, Hannover (DE)

( * ) Notice: Subject to any disclaimer, the term of this patent is extended or adjusted under 35 U.S.C. 154(b) by 0 days.

(21) Appl. No.: 10/086,635

(22) Filed: Mar. 4, 2002

(65) Prior Publication Data

US 2002/0173681 A1 Nov. 21, 2002

Related U.S. Application Data

(63) Continuation of application No. PCT/EP00/08396, filed on Aug. 29, 2000.

(30) Foreign Application Priority Data

Sep. 4, 1999  (DE) .......................................... 199 42 373
Nov. 24, 1999 (DE) .......................................... 199 56 365

(51) Int. Cl.$^7$ .............................. C01B 7/19; C01B 7/01; B01J 38/62; B01J 20/34; C07C 17/00
(52) U.S. Cl. ........................ 423/483; 423/486; 423/507; 502/28; 502/36; 570/163; 570/164; 570/165; 570/170
(58) Field of Search ................................. 423/469, 481, 423/483, 486, 507; 585/904; 502/28, 36; 570/123, 134, 170, 163–165

(56) References Cited

U.S. PATENT DOCUMENTS

| | | | |
|---|---|---|---|
| 4,003,984 A | | 1/1977 | Jones et al. ................. 423/168 |
| 4,372,938 A | | 2/1983 | Oda et al. .................... 423/469 |
| 4,734,526 A | * | 3/1988 | Albert et al. ................ 564/282 |
| 5,399,795 A | * | 3/1995 | Franz et al. ................. 570/165 |
| 5,498,807 A | * | 3/1996 | Schach et al. .............. 570/127 |
| 5,728,884 A | * | 3/1998 | Hahn et al. .................. 564/468 |
| 5,847,245 A | | 12/1998 | Franz et al. ................. 570/175 |
| 5,969,199 A | | 10/1999 | Franz et al. ................. 570/175 |

FOREIGN PATENT DOCUMENTS

| | | |
|---|---|---|
| DE | 2823969 | 12/1979 |
| DE | 19942374 | 5/2000 |
| DK | 2442883 | 3/1976 |
| DK | 2460821 | 6/1976 |
| EP | 0005810 | 12/1979 |
| EP | 0901999 | 3/1999 |
| WO | 00/32549 | 6/2000 |
| WO | 01/17931 | 3/2001 |

OTHER PUBLICATIONS

Jens Chr. Norrild, et al., "A Facile and Efficient Synthesis of (+)- and (-)-allo- Muscarine and Analogs", Short Papers, Mar. 14, 1997.

R. F. Weinland, et al., "Over hydraulic fluorides of some, partially very weak, organic Basen" Agrikulturchemisches Laboratorium, Oct. 1908.

Wolski, et al., Journal of American Chemistry Society, vol. 72, 1950, pp. 995–997.

Padma, et al., Indian Journal of Chemistry, vol. 20A, 1981, pp. 777–779.

Franz, Journal of Fluorine Chemistry, vol. 15, 1980, pp. 423–434.

Prakash, et al., Indian Journal of Chemistry, vol. 20, 1981, pp. 195–197.

* cited by examiner

Primary Examiner—Wayne A. Langel
Assistant Examiner—Jonas N. Strickland
(74) Attorney, Agent, or Firm—Crowell & Moring LLP

(57) ABSTRACT

Hydrogen fluoride adducts and ammonium fluorides are used for fluorinating acid chlorides and halocarbon compounds such as chloroalkanes or chlorinated ethers. The used adducts can be regenerated and then reused in the fluorination reactions.

13 Claims, No Drawings

REGENERATION OF ONIUM FLUORIDE-HF ADDUCTS

CROSS REFERENCE TO RELATED APPLICATIONS

This application is a continuation of international patent application no. PCT/EP00/08396, filed Aug. 29, 2000, designating the United States of America, the entire disclosure of which is incorporated herein by reference. Priority is claimed based on Federal Republic of Germany application nos. DE 199 42 373.3, filed Sept. 4, 1999, and DE 199 56 365.9, filed Nov. 24, 1999.

BACKGROUND OF THE INVENTION

The invention relates to a method for regenerating spent ammonium fluoride-HF adducts. Adducts of ammonium fluorides and HF can be used as fluorination reagents. European patent application no. EP-A 901,999, for example, describes the production of sevoflurane from the corresponding fluorinated ether, using HF and an amine. The work-up is performed with the addition of water, with the result that the onium fluoride-HF adduct is destroyed.

U.S. Pat. No. 4,372,938 describes the production of $SF_4$ using ammonium fluoride adducts. The spent onium fluoride-HF adducts are regenerated by contacting with hydrogen fluoride and are reused in the production of $SF_4$. The amines used are nitrogen-containing, heterocyclic aromatic compounds.

SUMMARY OF THE INVENTION

The object of the present invention is to provide an improved regeneration method.

It is also an object of the invention to provide a regenerated $NH_3$ or amine-HF adduct product.

These and other objects are achieved by providing an improved process for producing fluorine-containing compounds from chlorine-containing or bromine-containing compounds by chlorine-fluorine exchange or bromine-fluorine exchange using an onium fluorid-HF adduct as a reagent or catalyst, in which spent onium fluoride-HF adduct is regenerated using HF in the presence of a liquid carboxylic acid; or a spent trialklyammonium fluoride-HF adduct or a spent HF adduct of a cyclic saturated amine is regenerated using HF.

According to the inventive method for producing fluorine-containing compounds from chlorine-containing or bromine-containing compounds by chlorine-fluorine exchange or bromine-fluorine exchange using onium fluoride-HF adducts as reagent or catalyst, spent onium fluoride-HF adducts are regenerated continuously or batchwise using HF in the presence of a liquid carboxylic acid, and/or spent trialklyammonium fluoride-HF adducts or spent HF adducts of cyclic saturated amines are regenerated using HF.

As used herein, the term "spent" means that the ratio of amine to HF has become unacceptably high and/or the HCl or HBr content has become unacceptably high. In the regeneration, the content of HCl (or HBr) in particular is reduced to an acceptable level—for example, to less than 1 mole HCl per mole amine or $NH_3$. In this respect, the HF content can be brought to the desired level by the addition, evaporation, or admixture of adducts with suitable concentrations.

It is advantageous to carry out the regeneration in an autoclave or pressurized vessel with the addition of HF at an elevated temperature ranging from 80 to 120° C., for example. The HCl or HBr that is liberated can be removed from the gas phase after the autoclave is opened. As an example, inert gas can be passed through the autoclave to remove the gas phase.

It has been shown to be advantageous if substantially all the HF for the fluorination is not consumed during the fluorination reaction. Although regeneration can be carried out even if the adduct has been essentially completely converted to ammonium chloride or onium chloride, or to the corresponding bromide, the regeneration is easier to perform when the ratio of amine to HF does not fall below 1 during the fluorination reaction.

Of course, the ratio of amine to hydrogen fluoride may be adjusted in the regenerated product. For many applications it is desirable for the ratio of amine to hydrogen fluoride in the adduct to lie between 1:1.1 and 1:3.5, preferably between 1:2 and 1:3. This can be achieved, for example, by removing the excess hydrogen fluoride in the regenerated product by heating or distillation.

According to U.S. Pat. No. 4,472,938, it is preferred to used ammonium fluoride-HF adducts based on nitrogen-containing aromatic compounds, such as pyridinium fluoride-HF adducts, in the production of sulfur tetrafluoride. In the regeneration method without addition of acid according to the present invention, an embodiment provides for the use of spent trialkylammonium fluoride-HF adducts or HF adducts of cyclic saturated amines. Such compounds are advantageously used in the regeneration method, in that it has been determined that spent trimethylammonium fluoride-HF or triethylammonium fluoride-HF adducts, and thus adducts of amines containing short alkyl chains, readily liberate HCl during regeneration. Spent trialkylammonium fluoride-HF adducts containing alkyl groups that have at least three carbon atoms are less prone to form solids. Naturally, this is an advantage for regeneration without the addition of acid. In addition, spent HF adducts of amines in which the nitrogen is contained in a saturated 5- or 6-member ring system and which also contain heteroatoms such as oxygen—adducts of piperidine or pyrrolidine, for example—can be regenerated in this manner.

When acid is not added, the regeneration of spent trimethylamine-HF adducts, triethylamine-HF adducts, tripropylamine-HF adducts, and tributylamin-HF adducts is especially preferred.

In accordance with one variant of the process of the invention, the spent adducts are regenerated by the addition of a liquid carboxylic acid (this term also includes dicarboxylic acids and tricarboxylic acids). Carboxylic acids, especially those containing a total of 2 to 4 carbon atoms, are preferably substituted by halogen atoms, in particular fluorine atoms. Trifluoroacetic acid is especially preferred as an additive.

Adducts containing short-chain alkyl groups have a tendency to form solids; this can be counteracted by using a liquid carboxylic acid, particularly trifluoroacetic acid. For spent adducts of amines containing long-chain alkyl groups, it is necessary to expel the contained HCl when the operation involves addition of a carboxylic acid. It is often sufficient to add up to 10 mol % of the acid, relative to the spent onium-HF adduct calculated as 100 mol %. Of course, even more acid may be added, up to 20 mol % or more, for example. 80 mol % is regarded as the upper limit, since side reactions may occur when more than 80 mol % acid is added.

According to a very particularly preferred embodiment, spent trialkylammonium fluoride-HF adducts, independent of the length of the alkyl groups on the nitrogen, are regenerated by adding a liquid carboxylic acid, preferably trifluoroacetic acid. The reduced tendency toward formation of solids and the easy expulsion of HCl gas are advantageous.

The method according to the invention with the addition of acid can generally be used to regenerate HF adducts of ammonia and amines. These amines may be primary, secondary, or tertiary amines. The substituents are preferably linear or branched alkyl groups containing 1 to 12 carbon atoms. Adducts of cyclic amines such as pyrrolidine, N-methylpyrrolidine, or piperidine may be used as well. In addition, amines with aromatic substituents such as aniline, or amines containing nitrogen in an aromatic ring system such as pyridine, may be regenerated. The regeneration method is particularly well suited for HF adducts of the aforementioned cyclic or aromatic amines as well as for secondary and tertiary amines, especially when these secondary and tertiary amines are substituted with 1 to 5, preferably 2 to 4 carbon atoms per substituent. Methyl, ethyl, n-propyl, i-propyl, n-butyl, and i-butyl are preferred substituents.

The method according to the invention allows the reuse of spent HF adducts of ammonia and amines from fluorination reactions. The regeneration method according to the invention may be used to regenerate spent adducts from the production of, for example, acid fluorides from acid chlorides, such as the production of carboxylic acid fluorides or sulfuryl fluoride from the corresponding chlorides. This applies also to spent adducts originating from the production of fluoroalkyl groups from chloroalkyl groups. Examples of such reactions include the production of fluoro(hydro) carbons, fluorochloro(hydro)carbons, and the analogous bromine derivatives from the corresponding chlorine compounds obtained by fluorine-chlorine exchange or fluorine-bromine exchange. Another example of such reactions is the production of fluoroalkyl ethers from the corresponding chloro- or bromoalkyl ethers.

A particular embodiment relates to regeneration for multi-step fluorination methods. For many multi-step fluorination methods, the conditions for the required reaction medium are different. This is the case for the production of sulfuryl fluoride from sulfuryl chloride, for example. It has been found that the second fluorination step, that of converting the sulfuryl chlorofluoride to sulfuryl fluoride, proceeds satisfactorily only if the sulfuryl chlorofluoride starting compound is obtained from an adduct of onium fluoride and HF in which the ratio of amine to hydrogen fluoride does not exceed 1:3.5. In contrast, the first step involving the fluorination of sulfuryl chloride to produce sulfuryl chlorofluoride is independent of the hydrogen fluoride content in the reaction medium.

In accordance with one specific embodiment of the invention, it is proposed to simultaneously perform the regeneration of spent adduct in cases where the hydrogen fluoride content in the reaction medium is not important. For the production of sulfuryl fluoride, spent adduct is regenerated in a first reactor using a large excess of HF while the sulfuryl chloride present in the reactor is simultaneously fluorinated to produce sulfuryl chloride fluoride. In this regard, it is not necessary to convert all the sulfuryl chloride. After regeneration, the hydrogen fluoride is distilled off to bring the amine to HF ratio to the desired value of less than 1:3.5. The reactor contents can either be further reacted to produce sulfuryl fluoride or transferred to another reactor to carry out this reaction.

The following examples are intended to further illustrate the invention without limiting its scope. The examples demonstrate that not only HF adducts with varying HCl content, but also even pure hydrogen chloride may be regenerated. A complete regeneration in the sense that HCl is completely eliminated is not necessary, but it is possible. Working examples show that also HF adducts with residual HCl content can in fact be used as a fluorination catalyst or fluorination agent.

The invention also relates to a regenerated product corresponding to the formula $NH_3 \times (1.1-9)\ HF \times (0.001-1)\ HCl$ or $amine \times (1.1-9)\ HF \times (0.001-1)\ HCl$. A product containing 1.1 to 3 HF and 0.001 to 0.5 HCl is preferred. "Amine" stands for $NR_3$, where $R=C_1$ to $C_4$ alkyl groups.

EXAMPLE 1

Recycling of $NBu_3 \times 1.7\ HCl$ to $NBu_3 \times Y\ HF$ using little HF

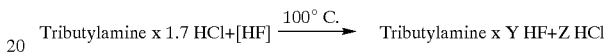

Charge

| Substance | Molar mass | Mass in g | Mole(s) |
| --- | --- | --- | --- |
| Tributylamine × 1.7 HCl | 247.34 | 82.17 | 0.33 |
| HF | 20.01 | 50 | 2.5 |

Tributylamine×1.7 HCl was placed in a laboratory autoclave. After the autoclave was sealed, 50 g HF was added, and the reagents were refluxed for approximately 3 hours at an internal reactor temperature of 100° C. The autoclave was then cooled to an internal reactor temperature of approximately 60° C., and the gas phase at or below atmospheric pressure in the autoclave was conducted into a wash bottle containing water.

According to the chloride and fluoride analysis of the wash bottle, the catalyst remaining in the autoclave had a composition of tributylamine×0.62 HCl×7.3 HF.

This example shows that even HF adduct that is completely spent during the formation of hydrochloride can be regenerated. It was possible to reuse the regenerated catalyst in the fluorination reaction. The following example shows that the HCl content of this product can be reduced even further.

EXAMPLE 2

Further reduction of the HCl content in $NBu_3 \times 0.62\ HCl \times 7.3\ HF$ to $NBu_3 \times Y\ HF$ using an excess of HF

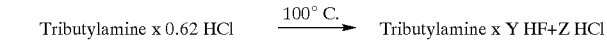

Charge

| Substance | Molar mass | Mass in g | Mole(s) |
| --- | --- | --- | --- |
| Tributylamine × 0.62 HCl × 7.3 HF | 354.3 | 116.83 | 0.33 |
| HF | 20.01 | 107 | 5.35 |

To the remaining mixture of tributylamine×0.62 HCl×7.3 HF was added anew 107 g HF, and the reagents were heated overnight at approximately 100° C. The autoclave was then cooled to an internal reactor temperature of approximately 60° C., and the gas phase at or below atmospheric pressure was conducted into a wash bottle containing water. Calculated according to the chloride and fluoride analysis of the wash bottle, the catalyst remaining in the autoclave had a composition of tributylamine×0.005 HCl×4.89 HF. This composition was confirmed by direct analysis of the remaining residue in the autoclave, showing that the HCl had been essentially completely driven off. Decomposition products of the amine were not detected. The resulting composition was of excellent quality for use as a fluorination reagent and fluorination catalyst.

EXAMPLE 3

Recycling of NEt₃×1.0 HCl to NEt₃×Y HF using an excess of HF

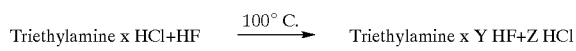

Charge

| Substance | Molar mass | Mass in g | Mole(s) |
|---|---|---|---|
| Tributylamine × HCl | 137.65 | 37.93 | 0.28 |
| HF | 20.01 | 107.7 | 5.38 |

Procedure

Triethylamine hydrochloride was placed in a laboratory autoclave which was then sealed. HF was then added, and the reagents were heated overnight at an internal reactor temperature of 100° C. At a reactor temperature of 100° C., the gas phase at or below atmospheric pressure was then conducted into a wash bottle filled with water. Calculated according to the chloride and fluoride analysis of the wash bottle, the catalyst remaining in the autoclave had a composition of triethylamine×0.09 HCl×5.35 HF. This composition was confirmed by direct analysis of the remaining residue in the autoclave, showing that the HCl had been essentially completely driven off. Decomposition products of the amine were not detected.

EXAMPLE 4

Adjustment of the amine/HF ratio of the catalyst mixture of Example 3 to 2.8–Removal Procedure The triethylamine×0.09 HCl×5.35 HF mixture obtained in Example 3 was introduced into a PFA (perfluoroalkyl) flask with frits, and the excess HF was driven off with dry nitrogen. After the weight of the flask had remained constant for 30 minutes, the flask was placed under a vacuum of $10^{-3}$ mbar for 10 minutes to completely remove all residual HF. According to chloride, fluoride, and amine analysis, the resulting catalyst had a composition of triethylamine×2.8 HF. HCl was no longer detectable. This clearly demonstrates the recyclability of the catalyst.

The adjustment of the amine to HF ratio restored the nucleophilic properties of the adduct. The product was of excellent quality for use as a reagent in the production of $SO_2F_2$ from $SO_2Cl_2$.

EXAMPLES 5 and 6
Variation of the duration of regeneration

EXAMPLE 5

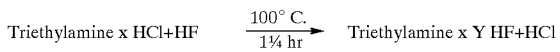

Charge

| Substance | Molar mass | Mass in g | Mole(s) |
|---|---|---|---|
| Tributylamine × HCl | 137.65 | 10.00 | 0.07 |
| HF | 20.01 | 16.5 | 0.82 |

Procedure

Triethylamine hydrochloride was placed in a laboratory autoclave which was then sealed. HF was then added, and the reagents were heated for 1¼ hours at a reactor temperature of approximately 100° C. (the autoclave was preheated for 15 minutes). The gas phase was then discharged into a stationary oil bath over a period of 15 minutes and analyzed (sample 1). The reactor contents (18.07 g) were transferred to a PFA flask and flushed with nitrogen for 5 minutes (18.02 g). 1.54 g was taken from this solution and brought to 1 L by filling with distilled water, then analyzed by wet chemical methods (sample 2).

According to the analytical data the catalyst composition was
NEt₃×5.75 HF×0.08 HCl.

EXAMPLE 6

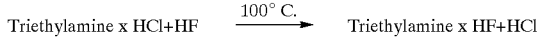

Charge

| Substance | Molar mass | Mass in g | Mole(s) |
|---|---|---|---|
| Tributylamine × HCl | 137.65 | 10.44 | 0.08 |
| HF | 20.01 | 21.3 | 1.06 |

Procedure

Triethylamine hydrochloride was placed in a laboratory autoclave which was then sealed. HF was then added, and the reagents were heated for 30 minutes at a reactor temperature of approximately 100° C. (the autoclave was preheated for 15 minutes). The autoclave was then taken from the oil bath, and the gas phase was discharged over a period of 15 minutes and analyzed (sample 1). The reactor contents (20.96 g) were transferred to a PFA flask and flushed with nitrogen for 5 minutes (20.64 g). 1.1 g was taken from this solution and brought to 1 L by filling with distilled water, then analyzed by ion chromatography (sample 2). According to the analytical data the catalyst composition was Triethylamine×8.48 HF×0.14 HCl.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. In a process for producing fluorine-containing compounds from chlorine-containing or bromine-containing compounds by chlorine-fluorine exchange or bromine-fluorine exchange using an onium fluoride-HF adduct as a reagent or catalyst, the improvement comprising regenerating spent onium fluoride-HF adduct using HF in the presence of a liquid carboxylic acid; or regenerating a spent trialklyammonium fluoride-HF adduct or a spent HF adduct of a cyclic saturated amine using HF.

2. A process according to claim 1, wherein the regenerating is carried out continuously.

3. A process according to claim 1, wherein the regenerating is carried out batchwise.

4. A process according to claim 1, wherein a spent onium fluoride-HF adduct which contains HCl or HBr is regenerated, and the HCl or HBr is driven off during the regeneration.

5. A process according to claim 4, wherein the HCl or HBr is carried off by passing an inert gas through or over the spent adduct.

6. A process according to claim 1, wherein the regeneration is carried out at a temperature in the range from −20 to 200° C.

7. A process according to claim 1, wherein the ratio of amine to HF during regeneration is adjusted to a value between 1:1.1 and 1:3.5.

8. A process according to claim 1, wherein the spent onium fluoride-HF adduct originates from production of an acid fluoride from a corresponding acid chloride.

9. A process according to claim 1, wherein the spent onium fluoride-HF adduct originates from the production of a fluoroalkanes from a chloroalkane.

10. A process according to claim 1, wherein the spent onium fluoride-HF adduct originates from production of a fluorinated ether from a chlorinated ether.

11. A process according to claim 1, wherein the regeneration is carried out simultaneously with a fluorination reaction using HF as fluorination reagent.

12. A process according to claim 1, wherein the regeneration is carried out in the presence of a halogenated carboxylic acid.

13. A process according to claim 12, wherein the regeneration is carried out in the presence of trifluoroacetic acid.

* * * * *